United States Patent [19]

Carmichael

[11] Patent Number: 5,728,518
[45] Date of Patent: Mar. 17, 1998

[54] ANTIVIRAL POLY-AND OLIGONUCLEOTIDES

[75] Inventor: Ellen Carmichael, West Hartford, Conn.

[73] Assignee: The Immune Response Corporation, Carlsbad, Calif.

[21] Appl. No.: 287,337

[22] Filed: Aug. 8, 1994

Related U.S. Application Data

[63] Continuation-in-part of Ser. No. 181,557, Jan. 12, 1994, abandoned.

[51] Int. Cl.[6] ............... C12Q 1/70; C12Q 1/68; G01N 33/53; C07H 21/04
[52] U.S. Cl. ............. 435/5; 435/6; 435/7.1; 536/23.1; 536/24.5
[58] Field of Search ............... 424/227.1; 435/91.1, 435/172.3, 172.1, 370, 5, 6, 7.1; 536/24.5, 23.1

[56] References Cited

U.S. PATENT DOCUMENTS

| | | | |
|---|---|---|---|
| 5,023,243 | 6/1991 | Tullis | 514/44 |
| 5,166,320 | 11/1992 | Wu et al. | 530/395 |
| 5,610,050 | 3/1997 | Blum et al. | 435/238 |

FOREIGN PATENT DOCUMENTS

| | | |
|---|---|---|
| 0 092 574 | 11/1983 | European Pat. Off. |
| 0 331 939 | 9/1989 | European Pat. Off. |
| 0 532 258 | 3/1993 | European Pat. Off. |
| WO 89/07136 | 8/1989 | WIPO |
| WO 91 04753 | 4/1991 | WIPO |

OTHER PUBLICATIONS

Wu and Wu. Specific Inhibition of Hepatitis B Viral Gene Expression in Vitro by Targeted Antisense Oligonucleotides. The Journal of Biological Chemistry. 267(18) pp. 12436–12439, Jun. 25, 1992.

Stein and Cheng. Antisense Oligonucleotides as Therapeutic Agents–is the Bullet Really Magical?. Science 261: 1004–1012, Aug. 20, 1993.

Wagner et al., "Influenza virus hemagglutinin HA–2 N–terminal fusogenic peptides augment gene transfer by transferrin–polylysine–DNA complexes: Toward a synthetic virus–like gene–transfer vehicle" *Proceedings of the National Academy of Sciences*, vol. 89, No. 17, pp. 7934–7938, Sep. 1992.

(List continued on next page.)

*Primary Examiner*—David Guzo
*Assistant Examiner*—William Sandals
*Attorney, Agent, or Firm*—Lahive & Cockfield, LLP; Jane E. Remillard; Giulio A. DeConti, Jr.

[57] ABSTRACT

Poly- and oligonucleotides which inhibit viral replication, particularly hepatitis virus replication, such as hepatitis B virus (HBV) replication, are disclosed. Preferred antiviral oligonucleotides include the following: an antiviral poly- or oligonucleotide which hybridizes to at least a portion of an RNA primer-binding region of a viral nucleic acid, preferably a DRII region of HBV DNA; an antiviral poly- or oligonucleotide which hybridizes to at least a portion of an RNA primer which binds a viral nucleic acid, preferably a DRII region of HBV DNA; an antiviral poly- or oligonucleotide which hybridizes to a hepatitis virus mRNA encoding a DNA polymerase, preferably an HBV mRNA; an antiviral poly- or oligonucleotide which hybridizes to a hepatitis virus mRNA encoding an envelope protein essential for viral attachment to a target cell, preferably an HBV mRNA encoding a pre-S1 protein; and an antiviral poly- or oligonucleotide which hybridizes to an encapsidation signal of a viral nucleic acid, preferably an HBV cis-encapsidation signal, thereby inhibiting encapsidation of the viral nucleic acid. The disclosed poly- or oligonucleotides can be used for detection of the presence of viral nucleic acid, particularly HBV DNA, in a cell and can be used to treat viral infection in a subject.

20 Claims, 3 Drawing Sheets

OTHER PUBLICATIONS

Wagner et al., "Transferrin-polycation conjugates as carriers for DNA uptake into cells" *Proceedings of the National Academy of Sciences*, vol. 87, pp. 3410–3414, May 1990.

Will et al., "Replication Strategy of Human Hepatitis B Virus" *Journal of Virology*, vol. 61, No. 3, pp. 904–911, Mar. 1987.

Wu et al., "Delivery systems for gene therapy" *Biotherapy*, vol. 3, pp. 87–95, 1991.

Wu et al., "Targeting Genes: Delivery and Persistent Expression of a Foreign Gene Driven by Mammalian Regulatory Elements In Vitro" *The Journal of Biological Chemistry*, vol. 264, No. 29, pp. 16985–16987, Pctober 15, 1989.

Wu et al., "receptor–mediated Gene Delivery and Expression in Vivo" *The Journal of Biological Chemistry*, vol. 263, No. 29, pp. 14621–14624, Oct. 15, 1988.

Wu et al., "Evidence for Targeted Gene Delivery to Hep G2 Hepatoma Cells in Vitro" *Biochemistry*, vol. 27, pp. 887–892, 1988.

Wu et al., "Receptor–mediated in Vitro Gene Transformation by a soluble DNA Carrier System" *The Journal of Biological Chemistry*, vol. 262, No. 10, pp. 4429–4432, Apr. 5, 1987.

Zenke et al., "Receptor–mediated endocytosis of transferrin–polycation conjugates: An efficient way to introduce DNA into hematopoietic cells" *Proceedings of the National Academy of Sciences*, vol. 87, pp. 3655–3659, May 1990.

Bartenschlager et al. (1990), "The P Gene Product Of Hapatitis B Virus Is Required As A Structural Component for Genomic RNA Encapsidation", *Journ. of Virology*, vol. 64, pp. 5324–5332.

Calvert et al. (1994), "Two Regions of An Avian Hepadnavirus RNA Pregenome Are Required In Cis for Encapsidation", *Journ. of Virology*, vol. 68, pp. 2084–2090.

Junker–Niepmann et al. (1990), "A Short Cis–Acting Sequence Is Required For Hepatitis B Virus Pregenome Encapsidation and Sufficient For Packaging of Foreign RNA", *The EMBO Journ.*, vol. 9, pp. 3389–3396.

Laskus et al. (1994), "The Stem–Loop Structure Of The Cis–Encapsidation Signal Is Highly Conserved In Naturally Occurring Hepatitis B Virus Variants", *Journ. of Virology*, vol. 200, pp. 809–812.

Pollack et al. (1993), "An RNA Stem–Loop Structure Directs Hepatitis B Virus Genomic RNA Encapsidation", *Journ. of Virology*, vol. 67, pp. 3254–3263.

Wu et al. (1992) "Specific Inhibition Of Hepatitis B Viral Gene Expression In–vitro By Targeted Antisense", *J. Biol. Chem* 267(18):12436–12439.

ANTIVIRAL POLY- AND OLIGONUCLEOTIDES

RELATED APPLICATION

This application is a Continuation-In-Part application of U.S. Ser. No. 08/181,557, filed Jan. 12, 1994 now abandoned, the contents of which are incorporated herein by reference.

BACKGROUND OF THE INVENTION

Poly- or oligonucleotides can be used to detect the presence of a particular virus in a cell and to specifically inhibit replication of the virus. These antiviral poly- or oligonucleotides can hybridize to and inhibit the function of an RNA, such as a messenger RNA, by physically blocking the binding of ribosomes or other proteins, thus preventing translation of the RNA. Antiviral poly-or oligonucleotides can also bind to and inactivate particular regions of DNA which are responsible for DNA replication. For example, U.S. patent application Ser. No.: 07/906,881 now abandoned, discloses antisense oligonucleotides complementary to various regions of a viral genome useful for inhibiting replication of the virus; U.S. patent application Ser. No 07/806,710 now abandoned, discloses antiviral antisense oligomers consisting of at least 2 nucleomonomers coupled through a substitute linkage, useful for binding to a selected RNA sequence; European Patent No; 532,258, discloses oligonucleotides comprising hepatitis and virus nucleotide sequences useful for detecting the virus and predicting the response to drug therapy.

Antiviral oligonucleotides can be in the form of small, chemically synthesized DNA or RNA oligonucleotides, or can be larger RNAs, such as mRNAs, biosynthetically generated in vitro or in vivo by transcription of a gene. RNA oligonucleotides include RNAs with catalytic activity (ribozymes), which can selectively bind to complementary sequences on a target RNA and physically destroy the target by mediating a cleavage reaction.

One area in which antiviral oligonucleotide therapy holds great promise is in fighting hepadnaviral infections, particularly hepatitis B viral (HBV) infections. Hepadnaviruses are small DNA viruses whose replication proceeds by reverse transcription of an RNA intermediate or pregenome, the precursor to the DNA form of the genome. Reverse transcription occurs principally within subviral particles (or cores) composed of the viral nucleocapsid protein (C), the polymerase (P), and the RNA pregenome. Encapsidation of HBV pregenomic RNA into core particles is highly selective. A variety of other HBV viral transcripts of both genomic and subgenomic lengths are also produced from the DNA genome, but are not encapsidated. Selective encapsidation of the RNA pregenome is now known to be dependent on both C and P gene products and on a cis-acting encapsidation signal, termed ε, which is highly conserved among all strains of HBV. The ε region is a 94 nucleotide sequence present on the 5' end of the RNA pregenome (Bartenschlager et al. (1990) *J Virol.* 64: 5324–5332; Junker-Niepmann et al. (1990) *EMBO J.* 9: 3389–3396; Pollack et al (1993) *J. Virol.* 67:3254–3263 (1993); Laskus et al. (1994) *Virology* 200: 809–812; Calvert et al. (1994) *J. Virol.* 68(4): 2084–2090). The ε sequence forms a stable RNA stem-loop structure which is essential for packaging activity. Once ecapsidated, the RNA pregenome is reverse transcribed to produce an HBV DNA genome which is capable of integration into host DNA. The process of reverse transcription includes an RNA priming reaction involving an eleven base repeated sequence, termed DRII, located near the 5' end of newly synthesized HBV minus-strand DNA. After the DNA minus-strand has been reverse transcribed from the pre-genome RNA, a 17 base segment of the pre-genome RNA (termed DRI) breaks off and binds to the DRII region of the DNA minus-strand to prime the synthesis of a DNA plus-strand. (See e.g., Will, W. et al. (1987), *J. of Virol.*, 61:904–911).

Currently, the majority of approaches to treat hepadnavirus infections, such as HBV-infections, are focused on the use of nucleoside analogs to inhibit viral DNA replication. However, nucleoside analogs have the drawback of being toxic to cells. Antiviral oligonucleotides on the other hand are highly specific for a particular target sequence and therefore act as effective viral inhibitors with little or no harm to cells. Such antiviral oligonucleotides would be beneficial therapeutically to treat or prevent hepadnavirus infection.

SUMMARY OF THE INVENTION

This invention provides poly- and oligonucleotides which can be used to inhibit viral replication, particularly hepatitis virus replication. In a preferred embodiment of the invention, the poly- and oligonucleotides are used to inhibit hepatitis B virus (HBV), particularly human HBV replication.

One aspect of the invention provides an antiviral poly- or oligonucleotide which hybridizes to at least a portion of a viral RNA primer. Preferably, the poly- or oligonucleotide hybridizes to at least a portion of an RNA primer which binds a DRII region of HBV DNA. Such a preferred poly- or oligonucleotide comprises a nucleotide sequence shown in SEQ ID NO: 2.

Another aspect of the invention provides an antiviral poly- or oligonucleotide which hybridizes to at least a portion of an RNA primer-binding region of a viral nucleic acid. Preferably, the poly- or oligonucleotide hybridizes to at least a portion of a DRII region of HBV DNA. Such a preferred oligonucleotide comprises a nucleotide sequence shown in SEQ ID NO: 1.

Yet another aspect of the invention provides an antiviral poly- or oligonucleotide which hybridizes to at least a portion of an hepatitis virus mRNA encoding a DNA polymerase. In a preferred embodiment, the poly- or oligonucleotide hybridizes to HBV mRNA, particularly human HBV mRNA, encoding a DNA polymerase. Preferred poly- or oligonucleotides hybridize to a region of HBV mRNA which includes the initiation codon for translation of the HBV mRNA. One such preferred poly- or oligonucleotide comprises a nucleotide sequence shown in SEQ ID NO: 3.

This invention further provides a poly- or oligonucleotide which hybridizes to at least a portion of a hepatitis virus mRNA encoding an envelope protein essential for viral attachment to a target cell. In a preferred embodiment, the poly-or oligonucleotide hybridizes to at least a portion of an HBV mRNA encoding a pre-S1 protein. Preferred poly- or oligonucleotides hybridize to a region of an HBV mRNA encoding a pre-S1 protein which contains the initiation codon for translation of the mRNA. One such preferred poly- or oligonucleotide comprises a nucleotide sequence shown in SEQ ID NO: 4.

Another aspect of the present invention features a poly- or oligonucleotide which hybridizes to an encapsidation signal of a viral nucleic acid, thereby inhibiting encapsidation of the nucleic acid. In a preferred embodiment of the invention, the poly- or oligonucleotide hybridizes to at least a portion of an HBV cis-encapsidation signal. Such preferred poly- or oligonucleotides include, but are not limited to, polynucleotides comprising a nucleotide sequence shown in SEQ ID NOs: 5–8.

This invention also features a soluble molecular complex for delivering an antiviral poly- or oligonucleotide of the present invention to a cell, particularly an hepatocyte. The complex comprises the antiviral poly- or oligonucleotide complexed with a carrier conjugate comprised of a cell-specific binding agent, preferably a ligand for the asialoglycoprotein receptor, linked to a poly- or oligonucleotide-binding agent, preferably polylysine. Methods for introducing a poly- or oligonucleotide of the present invention to a cell in vivo, ex vivo, or in vitro are also disclosed.

The poly- or oligonucleotides of the invention can be used for detecting the presence of viral nucleic acid in a sample, particularly the presence of HBV DNA. The presently disclosed poly- or oligonucleotides can also be used to evaluate the efficacy of antiviral drugs by, for example, detecting the presence of viral replication intermediates in a cell. The poly- or oligonucleotides of the invention can further be used therapeutically to treat viral infections, particularly HBV infections.

BRIEF DESCRIPTION OF THE FIGURES

FIG. 2 also shows the regions of ε bound by antiviral oligonucleotides Loop (SEQ ID NO: 5), Bulge (SEQ ID NO: 6), Between (SEQ ID NO: 7), and Core (SEQ ID NO: 8).

DETAILED DESCRIPTION OF THE INVENTION

This invention pertains to poly- and oligonucleotides which hybridize to a viral nucleic acid to thereby inhibit viral replication. The poly- and oligonucleotides of the invention are particularly useful for inhibiting replication of human hepatitis B virus (HBV).

Accordingly, one aspect of this invention pertains to a poly- or oligonucleotide which hybridizes to at least a portion of an RNA primer-binding region of a viral nucleic acid or to a viral RNA primer. The term "viral RNA primer", as used herein, is intended to include RNAs which bind to a viral nucleic acid, preferably a single-stranded DNA, and serve as a primer for initiating synthesis of a complementary viral nucleic acid. The term "RNA primer-binding region", as used herein, refers to a region of a viral nucleic acid, and portions thereof, to which an RNA primer as defined herein binds. These regions can be identified by, for example, mapping the termini of the viral nucleic acid by primer extension and S1 nuclease protection analysis performed on deproteinated nucleic acid. The RNA primer-binding region includes at least those bases required for hybridization of an RNA primer. Standard genetic studies can be used to determine exactly which bases these include.

In a preferred embodiment of the invention, the RNA primer-binding region is a hepatitis virus nucleic acid, preferably a single-stranded HBV DNA comprising at least a portion of an HBV DRII region. In another preferred embodiment, the RNA primer is an HBV RNA primer which binds to an HBV DRII region.

Preferred poly- or oligonucleotides of the invention hybridize to at least a portion of a DRII region of HBV DNA or to at least a portion of an RNA primer which binds to a DRII region of HBV DNA, thereby substantially blocking or inhibiting the binding of the RNA primer to this region. Such preferred poly- or oligonucleotides include an oligonucleotide comprising a nucleotide sequence shown in SEQ ID NO: 2 (DRII(S)), which hybridizes to an RNA primer which binds to the DRII region, and an oligonucleotide comprising a nucleotide sequence shown in SEQ ID NO: 1 (DRII(R)), which hybridizes to the DRII region itself.

Another aspect of the invention provides a poly- or oligonucleotide which can be used to inhibit translation of a hepatitis virus mRNA encoding a DNA polymerase. In a preferred embodiment, the hepatitis virus is HBV, preferably human HBV. The phrase "hepatitis virus mRNA which encodes a DNA polymerase", as used herein, refers to a hepatitis gene transcript which is capable of translation into a functional DNA polymerase. Preferred poly- or oligonucleotides of the invention hybridize to at least a portion of an HBV mRNA encoding a DNA polymerase. This portion preferably includes the initiation codon for translation of the HBV mRNA. For example, a poly- or oligonucleotide of the invention can hybridize to and substantially block the internal AUG codon which initiates translation of an mRNA encoding an HBV DNA polymerase. One such preferred poly- or oligonucleotide has a nucleotide sequence shown in SEQ ID NO: 3.

Another aspect of the invention provides a poly- or oligonucleotide which can be used to inhibit translation of a hepatitis virus mRNA encoding an envelope protein essential for viral attachment to a target cell. The phrase "essential for viral attachment to a target cell", as used herein, refers to those hepatitis virus surface proteins which are responsible for attachment of the virus to its target cell. For example, HBV contains three such surface proteins, the pre-S1, pre-S2 and S proteins, all of which function to bind the virus to a target cell. In a preferred embodiment, the hepatitis virus mRNA is HBV mRNA, preferably an HBV mRNA which encodes a pre-S1 protein. Preferred poly- or oligonucleotides hybridize to at least a portion of an HBV pre-S1 mRNA which includes the initiation codon for translation of the mRNA. One such poly- or oligonucleotide has a nucleotide sequence shown in SEQ ID NO: 4.

Figure 1:
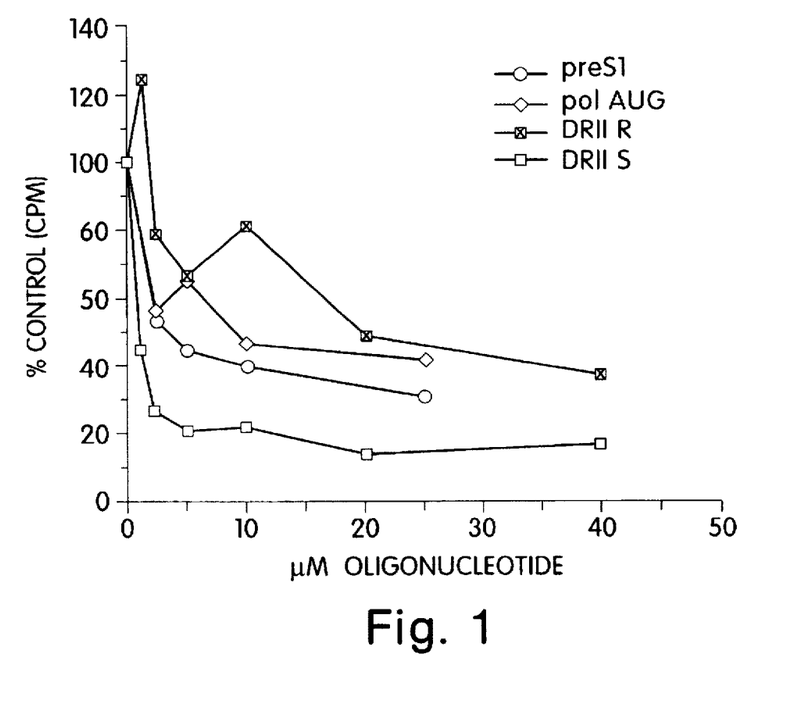
FIG. 1 is a graphic representation depicting the antiviral effect of oligonucleotides DRII(R) (SEQ ID NO: 1), DRII(S) (SEQ ID NO: 2), Pol-AUG (SEQ ID NO: 3), and Pre-S1 (SEQ ID NO: 4), as indicated by the decreased presence of intracellular and extracellular HBV replication intermediates from HBV infected cells.
Figure 2:
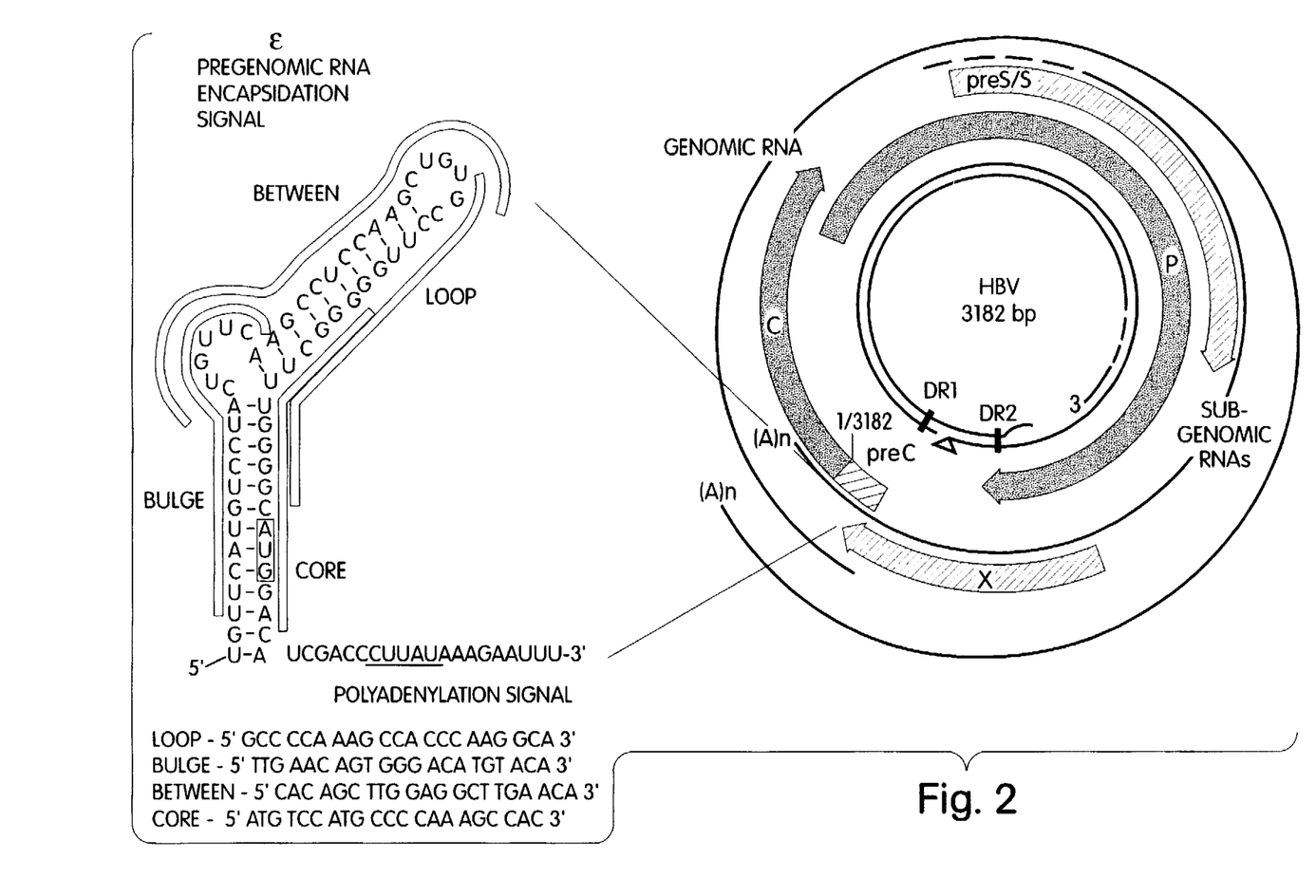
FIG. 2 shows the RNA sequence (SEQ ID NO: 9) and the stem-loop structure of the HBV cis-encapsidation signal (ε).
Figure 3:
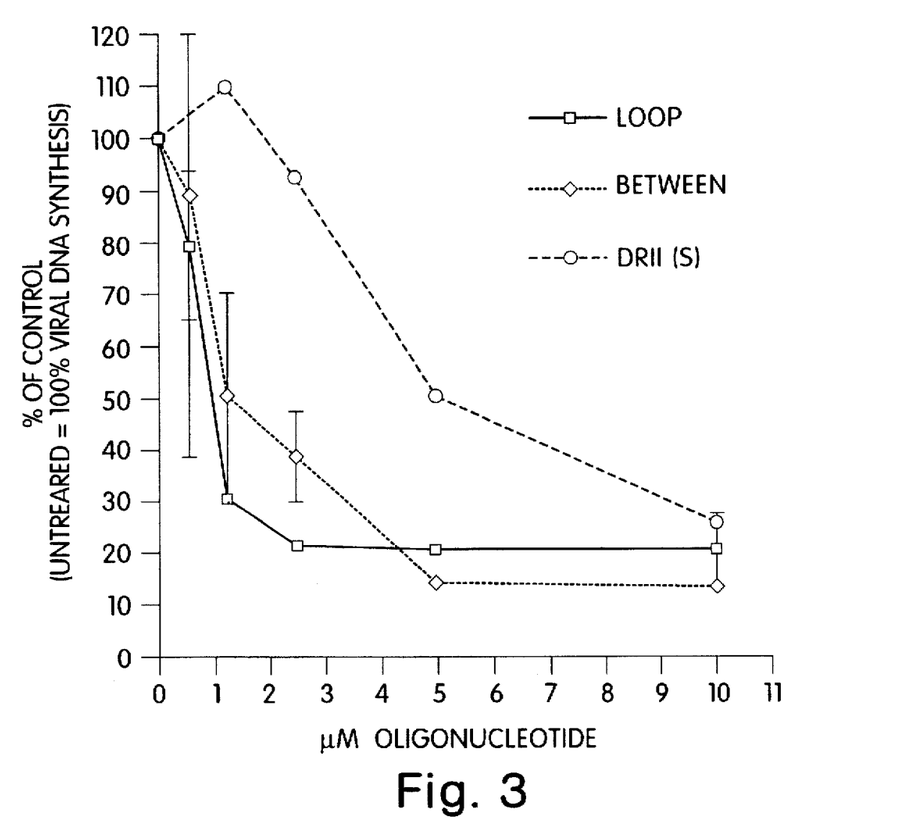
FIG. 3 is a graphic representation depicting the antiviral effect of soluble molecular complexes containing oligonucleotides DRII (SEQ ID NO: 1), Loop (SEQ ID NO: 5), and Between (SEQ ID NO: 7), as indicated by the decreased presence of intracellular and extracellular HBV replication intermediates from HBV infected cells.

This invention further provides a poly- or oligonucleotide which can be used to inhibit viral encapsidation. The term "viral encapsidation", as used herein, refers to the process by which a viral nucleic acid packaged into core particles, thereby producing a mature, infectious virion. Poly-or oligonucleotides of the invention hybridize to at least a portion of an encapsidation signal of a viral nucleic acid, thereby inhibiting encapsidation of the nucleic acid. The term "encapsidation signal", as used herein, refers to a nucleic acid molecule which includes those nucleotides necessary for viral encapsidation. Standard genetic studies, such as mutational analysis, can be used to determine exactly which bases these include (see e.g., Calvert et al. (1994) *J. Virol.* 68(4): 2084–2090); Laskus et al. (1994) *Virology* 200: 809–812). In a preferred embodiment of the invention, the encapsidation signal is a hepatitis virus encapsidation signal, preferably the HBV cis-encapsidation signal (ε). As shown in FIG. 3, the ε region is a short, 94 nucleotide sequence (Bartenschlager et al. (1990) *J Virol.* 64: 5324–5332; Junker-Niepmann et al. (1990) *EMBO J.* 9: 3389–3396; Calvert et al. (1994) *J. Virol.* 68(4): 2084–2090) which forms a stable RNA stem-loop structure that is required for viral encapsidation activity (Pollack et al. (1993) *J. Virol.* 67:3254–3263 (1993); Laskus et al. (1994) *Virology* 200: 809–812). Preferred poly- or oligonucleotides of the invention hybridize to ε, or a portion thereof, and disrupt the secondary structure of the ε region. This disruption causes significant inhibition of HBV pregenomic RNA packaging. Such preferred poly- or oligonucleotides of the present invention include, for example, poly- or oligonucleotides comprising a nucleotide sequence shown in FIG. 3 (SEQ ID NOs: 5–8).

The term "hybridize", as used herein, is intended to include hybridization under intracellular conditions.

The term "poly- or oligonucleotide", as used herein, is intended to include a single-stranded DNA or RNA molecule which hybridizes to at least a portion of a particular viral nucleic acid as defined herein under intracellular conditions. The degree of complementarity required for appropriately specific hybridization to a target viral nucleotide sequence under intracellular conditions can be determined empirically. Poly- or oligonucleotides of the invention can range in length from about 15 to about 32 bases. Preferred poly- or oligonucleotides range from about 20 to about 25 bases. Poly- and oligonucleotides of the invention are preferably directed against hepatitis B virus nucleic acids. However, nucleic acids from other strains of hepadnaviruses, such as hepatitis A and hepatitis C, which also contain RNA primer binding regions, Core and Polymerase genes, and encapsidation signals, can also be targeted. Poly- and oligonucleotides of the invention can also be directed against nucleic acids of viruses other than hepadnaviruses, such as herpes virus, or influenza virus, whose replication cycles include the production and use of polymerase or envelope proteins, encapsidation signals, or RNA primers.

In particular, poly- and oligonucleotides of the invention which hybridize to an RNA primer-binding region of a viral nucleic acid or to an RNA primer can be used to substantially block or inhibit viral replication which occurs by reverse transcription, such as retroviral replication. This is due to the nature of the reverse transcription reaction in which minus-strand DNA is the template for plus-strand DNA synthesis, thereby necessitating two separate priming reactions for the synthesis of each DNA strand. During retrovirus replication, plus-strand DNA synthesis is primed by an RNA oligomer derived from a segment of the viral RNA genome (Seeger et al. (1991), *Current Topics in Microbiology and Immunology*, 168: 41–60). Therefore retroviruses, such as those from the Oncovirinae family (e.g., Rous sarcoma virus, Moloney murine leukemia virus, Human T-cell leukemia virus), the Lentivirinae family (e.g., Human immunodeficiency virus, Simian immunodeficiency virus), and the Spumavirinae family (e.g., Simian foamy virus), to name but a few, also contain RNA primers and RNA primer-binding sites which can be blocked and inactivated by the poly- or oligonucleotides of the invention, thereby inhibiting viral replication.

The poly- or oligonucleotides of the invention can be chemically synthesized using standard techniques well known in the art. For example, various methods of chemically synthesizing polydeoxynucleotides are known, including solid-phase synthesis which, like peptide synthesis, has been fully automated in commercially available DNA synthesizers (See e.g., Itakura et al., U.S. Pat. No. 4,598,049; Caruthers et al., U.S. Pat. No. 4,458,066; and Itakura, U.S. Pat. Nos. 4,401,796 and 4,373,071, incorporated by reference herein).

However, when administered in vivo, synthetic and natural oligonucleotides are subject to degradation by exo- and endonucleases in a manner equivalent to any cellular nucleic acid. Accordingly, preferred oligonucleotides of the invention are chemically modified to provide substantial nuclease resistance. Such chemically modified oligonucleotides include, for example, phosphorothioate oligonucleotides, in which one of the phosphate oxygens is replaced by a sulfer atom (See e.g., U.S. Pat. No: 5,262,530, the teachings of which are incorporated by reference herein). Phosphorothioates may be synthesized using automated techniques employing either phosphoramidite or phosphonate chemistries. Other modified oligonucleotides with increased stability include, for example, nonionic DNA analogs, such as alkyl- or arylphosphonates, in which the charged phosphate oxygen is replaced by an alkyl or aryl group (see e.g., U.S. Pat. No: 4,469,863, the teachings of which are incorporated by reference herein), and alkylphosphotriesters, in which the charged oxygen moiety is alkylated (See e.g., U.S. Pat. No: 5,023,243 and European Pat. No: 092,574, the teachings of which are incorporated by reference herein). Both of these DNA analogs can be prepared by automated solid-phase synthesis using commercially available reagents. It is also known that addition of a diol, such as tetraethyleneglycol or hexaethyleneglycol, at either or both termini of a synthetic oligonucleotide confers substantial nuclease resistance. (See e.g., U.S. Pat. No: 5,245,022, the teachings of which are incorporated by reference herein).

Another aspect of the invention provides a soluble molecular complex for delivering poly- or oligonucleotides of the present invention to cells in vivo, ex vivo, or in vitro. The term "soluble", as used herein, means that the complex is soluble in solution so that it can easily pass through physiological barriers when administered in vivo to reach target cells or tissues. The molecular complex comprises a poly- or oligonucleotide of the invention complexed to a carrier conjugate comprised of a cell-specific-binding agent linked to a poly- or oligonucleotide-binding agent.

The cell-specific binding agent is a molecule which specifically binds a cellular surface structure which mediates its internalization into cellular endosomes by, for example, the process of endocytosis. The surface structure can be a protein, polypeptide, carbohydrate, lipid or combination thereof. It is typically a surface receptor which mediates endocytosis of a ligand. Thus, the binding agent can be a natural or synthetic ligand which binds the receptor. The ligand can be a protein, polypeptide, glycoprotein, glycopeptide or glycolipid which has functional groups that are exposed sufficiently to be recognized by the cell surface structure. It can also be a component of a biological organism such as a virus, cells (e.g., mammalian, bacterial, protozoan).

The cell-specific ligand can also be an antibody, or an analogue of an antibody such as a single chain antibody, which binds the cell surface structure.

Ligands useful in forming the carrier will vary according to the particular cell to be targeted. For targeting hepatocytes, galactose-terminal carbohydrates such as carbohydrate trees obtained from natural glycoproteins, especially structures that either contain terminal galactose residues or can be enzymatically treated to expose terminal galactose residues, can be used although other ligands such as polypeptide hormones may also be employed. In addition, naturally occurring plant carbohydrates such as arabinogalactan can be used as ligands. Other useful ligands for hepatocyte targeting include glycoproteins having exposed terminal carbohydrate groups such as asialoglycoproteins (galactose-terminal). These galactose-terminal ligands can be formed by coupling galactose-terminal carbohydrates such as lactose or arabinogalactan to nongalactose-bearing proteins by reductive lactosamination. Examples of additional asialoglycoproteins include, but are not limited to, asialoorosomucoid, asialofetuin and desialylated vesicular stomatitis virus. Such ligands can be formed by chemical or enzymatic desialylation of glycoproteins that possess terminal sialic acid and penultimate galactose residues.

For targeting the soluble molecular complex to other cell surface receptors, other types of ligands can be used, such as mannose for macrophages (lymphoma), mannose 6-phosphate glycoproteins for fibroblasts (fibro-sarcoma), intrinsic factor-vitamin B12 and bile acids (See Kramer et al. (1992) *J. Biol. Chem.* 267:18598–18604) for enterocytes, insulin for fat cells, and transferrin for smooth muscle cells. Alternatively, the cell-specific binding agent can be a receptor or a receptor-like molecule, such as an antibody which binds a ligand (e.g., antigen) on the cell surface. Such antibodies can be produced by standard procedures.

The polynucleotide-binding agent of the carrier conjugate complexes the polynucleotide to be delivered. Complexation with the polynucleotide must be sufficiently stable (either in vivo, ex vivo, or in vitro) to prevent significant uncoupling of the polynucleotide extracellularly prior to internalization by the target cell. However, the complex is cleavable under appropriate conditions within the cell so that the polynucleotide is released in functional form within the cell.

In a preferred embodiment, the binding between the polynucleotide-binding agent and the polynucleotide is based on electrostatic attraction which provides sufficient extracellular stability, but is releasable intracellularly. Preferred polynucleotide-binding agents are polycations that bind negatively charged polynucleotides. These positively charged proteins can bind noncovalently with the polynucleotide to form a targetable molecular complex which is stable extracellularly but releasable intracellularly. Suitable polycations are polylysine, polyarginine, polyornithine, basic proteins such as histones, avidin, protamines and the like. A preferred polycation is polylysine (e.g., ranging from 3,800 to 60,000 daltons). Other noncovalent bonds that can be used to releasably link the expressible polynucleotide include hydrogen bonding, hydrophobic bonding, electrostatic bonding alone or in combination such as, antipolynucleotide antibodies bound to polynucleotide, and streptavidin or avidin binding to polynucleotide-containing biotinylated nucleotides.

The carrier can be formed by chemically linking the cell-specific-binding agent and the poly- or oligonucleotide binding agent using methods and cross-linking reagents which are well known in the art. The linkage is typically covalent. A preferred linkage is a peptide bond. This can be formed with a water soluble carbodiimide, such as 1-ethyl-3-(3-dimethylaminopropyl)carbodiimide hydrochloride (EDC), as described by Jung, G. e.t al. (1981) *Biochem. Biophys. Res. Commun.*101: 599–606 or Grabarek et al. (1990) *Anal. Biochem.* 185: 131. Alternative linkages are disulfide bonds which can be formed using cross-linking reagents, such as N-Succinimidyl 3-(2-pyridyldithio) propionate (SPDP), N-hydroxysuccinimidyl ester of chlorambucil, N-Succinimidyl-(4-Iodoacetyl) aminobenzoate) (SIAB), Sulfo-SIAB, and Sulfo-succinimidyl-4-maleimidophenyl-butyrate (Sulfo-SMPB). Strong noncovalent linkages, such as avidin-biotin interactions, can also be used to link the cell-specific binding agent and the polynucleotide binding agent.

The linkage reaction can be optimized for the particular cell-specific-binding agent and poly- or oligonucleotide-binding agent used to form the carrier. Reaction conditions can be designed to maximize linkage formation but to minimize the formation of aggregates of a carrier component. As described below in Example 2, the optimal ratio of cell-specific-binding agent to poly- or oligonucleotide-binding agent can be determined empirically. When polycations are used, the ratio of the components will vary with the size of the polycation and the size of the poly- or oligonucleotide. In general, the ratio of poly- or oligonucleotide to carrier ranges from about 10:1 to 1:1, and is preferably about 2:1, by weight. Uncoupled components and aggregates can be separated from the carrier by molecular sieve or iron exchange chromatography (e.g., Aquapore™ cation exchange, Rainin).

In one embodiment of the invention, asialoorosomucoid-polylysine conjugate is formed with the cross linking agent 1-(3-dimethylaminopropyl)-3-ethyl carbodiimide. After dialysis, the conjugate is separated from unconjugated components by preparative acid-urea polyacrylamide gel electrophoresis (pH 4–5). The conjugate can be further purified on the carboxymethyl functionalized column (see U.S. patent application Ser. No.08/043,008, filed Apr. 5, 1993 now abandoned, the teachings of which are incorporated by reference herein).

The poly- or oligonucleotides of the invention can be used in methods of diagnosing and treating viral infections in a subject, such as hepatitis B viral infections. Accordingly, this invention also provides methods of introducing a poly- or oligonucleotide of the invention into a specific cell. In one embodiment, a poly- or oligonucleotide of the invention is administered to a subject, either in the form of a free poly- or oligonucleotide or in the form of a soluble molecular complex of the invention, in a pharmaceutically acceptable carrier. The term "subject", as used herein, is intended to include living organisms capable of viral infections including, for example, cats, dogs, rats, monkeys, and mice. The term "pharmaceutically acceptable carrier", as used herein, is intended to include any physiologically acceptable carrier for stabilizing poly- or oligonucleotides of the present invention for administration in vivo, including, for example, saline and aqueous buffer solutions, solvents, dispersion media, codines, antibacterial and antifungal agents, isotonic and absorption delaying agents, and the like. The use of such media and agents for pharmaceutically active substances is well known in the art. Except insofar as any conventional media or agent is incompatible with the an antiviral poly- or oligonucleotide of the present invention, use thereof in a therapeutic composition is contemplated.

The poly- or oligonucleotides of the invention can also be protected from degradative enzymes by encapsulation into liposomes. These delivery vehicles are comprised of one or more spherical lipid bilayers, typically phospholipid bilayers, which protect the drugs they encapsulate. Once administered to a subject, the liposomes are taken up by cells via endocytosis and the drugs they contain are released therein. (See e.g., WO 92/06192, the teachings of which are incorporated by reference herein).

For in vivo delivery to cells, polynucleotides of the present invention, either in the form of a free poly- or oligonucleotide or in the form of a soluble molecular complex of the invention, can be administered parenterally. Preferably, the poly- or oligonucleotide is injected intravenously in solution containing a pharmaceutically acceptable carrier as defined herein. Pharmaceutical compositions suitable for injectable use include sterile aqueous solutions (where water soluble) or dispersions and sterile powders for extemporaneous preparation of sterile injectable solutions or dispersions. In all cases, the composition must be sterile and must be fluid to the extent that easy syringability exists. It must be stable under the conditions of manufacture and storage and must be preserved against the contaminating action or microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various anti-bacterial and anti-fungal agents, for example, parabens, chlorobutanol, phenol, ascorbic acid, thimerosal, and the like. In many case, it will be preferable to include acetonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (i.e., a poly- or oligonucleotide of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders in the preparation of sterile injectable solutions, the preferred methods of preparation are vacuum drying and freeze-drying which yields a powder of the active ingredient (i.e., an antiviral poly- or oligonucleotide of the present invention in a pharmaceutically acceptable carrier) plus any additional desired ingredient from a previously sterile-filtered solution thereof.

For in vitro delivery of polynucleotides of the present invention, cultured cells can be incubated with the polynucleotide, either in the form of a free poly- or oligonucleotide or in the form of a soluble molecular complex of the invention, in an appropriate medium under conditions conducive to endocytotic uptake by the cells. Polynucleotides of the present invention can also be delivered ex vivo to cells or tissues which have been removed from an organism and will subsequently be returned to the organism.

A poly- or oligonucleotide of the invention when introduced to a cell infected with a virus is capable of inhibiting viral replication in the cell either in vitro or in vivo. In particular, HBV replication can be inhibited. The ability of a poly- or oligonucleotide of the invention to inhibit viral replication is determined by the absence of or reduction in intracellular viral replication intermediates and extracellular viral DNA (e.g., mature virions) following introduction of a poly- or oligonucleotide of the invention into a cell infected with a virus. For example, as described below in Example 1, the ability of a poly- or oligonucleotide of the invention to inhibit HBV replication is measured by a reduction in intracellular HBV single-stranded DNA and partial relaxed circle DNA replication intermediates, and by a reduction in extracellular HBV virions following introduction into the cell of the poly- or oligonucleotides.

Soluble molecular complexes containing ASOR-polylysine conjugate complexed with antisense oligonucleotides directed against HBV DNA have been successfully delivered to cells (i.e., hepatocytes) in vivo in HBV infected animal models. In particular, molecular complexes containing antisense oligonucleotides directed against the woodchuck hepatitis virus polyA signal and the core gene AUG (start) codon were administered to HBV infected woodchucks on five consecutive days in the form of single intravenous bolus injections. All four treated animals simultaneously exhibited a $\geq 0.5$–$1.0$ log decrease of viral DNA in serum (see Spitalny, G. L. et al. "Receptor-Mediated Delivery via a Protein Carrier of Antisense Oligonucleotides and Traditional Antiviral Drugs Applicable for the Treatment of Hepatitis Infection" Abstract presented at the International Society for Research's Feb. 27, 1994–Mar. 4, 1994 Seventh International Conference on Antiviral Research, Charleston, N.C.). Efficacy of the antiviral poly and oligonucleotides of the invention in animal models of viral infection, such as the HBV infected woodchucks, may be predictive of efficacy in humans.

Poly- or oligonucleotides of the present invention can also be used for diagnostic purposes, such as detecting the presence of a virus, particularly HBV, in an infected cell. Using standard hybridization techniques, the disclosed antiviral poly- or oligonucleotides can be used to screen for the presence of a particular virus. For example, total cellular DNA from cell cultures can be enzymatically digested and blotted according to standard Southern Blot techniques. Blots can then be probed with the presently disclosed antiviral poly- or oligonucleotides which hybridize to and allow detection of the presence of viral nucleic acid in the sample. In particular, the presence of hepatitis B viral DNA sequences can be detected.

The invention is further illustrated by the following examples which should not be construed as further limiting the subject invention. The contents of all references and published patent applications cited throughout this application are hereby incorporated by reference.

EXAMPLE 1

In Vitro HBV Antiviral Assay

Eight antiviral phosphorothiate oligonucleotides consisting of DRII(R) (SEQ ID NO: 1), DRII(S) (SEQ ID NO: 2), p-AUG (SEQ ID NO: 3), pre-S1 (SEQ ID NO: 4), Loop (SEQ ID NO: 5), Bulge (SEQ ID NO: 6), Between (SEQ ID NO: 7), and Core (SEQ ID NO: 8) were obtained from Midland Certified Reagent Co., Midland, Tex. The ability of these oligonucleotides to inhibit viral replication was assayed as follows.

(i) Cell Culture and antiviral drug treatment

Stock cultures of an HBV-DNA transfected human hepatoblastoma (HepG2)-derived cell line, 2.2.15 (Sells, M. A., et al., (1987) *Proc. Natl. Acad. Sci.* 84:1005–9; Sells, M. A., et al., (1988) *J. Virol.* 62:2336–44) was maintained in RPMI-1640 (GIBCO) supplemented with 5% fetal bovine serum and 2 mM L-glutamine. The cells were incubated at 37° C. in a moist atmosphere containing 5% $CO_2$. For antiviral treatment, 2.2.15 cells were seeded onto collagen-coated 24-well plates at a density of $4 \times 10^4$ cells/$cm^2$. Confluent cultures (6–8 days post-seeding) were incubated in RPMI-1640 medium supplemented with 2% fetal bovine serum and increasing concentrations of each oligonucleotide. The oligo-containing medium was added on day 1 (post-confluence) and replaced every 2 days (days 3, 5, 7, 9) with medium containing fresh oligonucleotide. On day 10, the medium and cells were collected for intracellular and extracellular HBV DNA analysis as follows.

(ii) Intracellular HBV DNA analysis

Total nucleic acid was extracted from antiviral oligonucleotide-treated 2.2.15 cultures as follows. Cells were washed two times with excess Tris-Buffered Saline. The monolayer was lysed in 400 μl of lysis buffer (0.6% SDS, 10 mM EDTA, 10 mM Tris-HCl pH 7.4) containing 20 μg/ml of RNase A and incubated at 37° C. for 30–60 minutes. The lysate was transferred to a microfuge tube, and proteinase K was added to a final concentration 100 μg/ml and incubated at 50° C. for at least 2 hours. After incubation, the lysate was adjusted to contain 300 mM NaOAc, extracted once with phenol/chloroform/isoamyl alcohol (25:24:1 v/v) and once with chloroform/isoamyl alcohol (24:1 v/v). The DNA was concentrated by ethanol precipitation, resuspended in 50 μl of TE (10 mM Tris HCl, pH 8.0/1 mM EDTA) and digested with the restriction enzyme Hind III. For Southern blotting a third of the digested DNA was electrophoresed in a 0.8% agarose gel and transferred to Micron Separations Systems Magna-Graph® nylon membrane by overnight capillary transfer using 10X SSC transfer buffer. Hybridization was performed at 68° C. with a [$^{32}$P]dCTP-labeled EcoRI fragment of pADW-HTD (provided by T. J. Liang) containing the full length 3.2 genome of HBV. All labeling reactions were carried out with the Random Primers DNA Labeling System (BRL, Life Technologies). Levels of integrated DNA, relaxed circle DNA and replication intermediates were quantitated using a Packard Instant Imager and were graphed as a percentage of the untreated control.

(iii) Extracellular HBV DNA analysis

For the analysis of extracellular DNA, the culture medium from the antiviral oligonucleotide-treated 2.2.15 cells was centrifuged in a microfuge for two minutes to remove cellular debris. To denature the extracellular DNA, 400 μl of the clarified medium was incubated for 20 minutes at room temperature (25° C.) in 1M NaOH/10X SSC (1X SSC is 0.15M NaCl/0.015M Sodium Citrate, pH 7.2). The samples were directly applied to nylon membranes (Micron Separations Systems "MAGNAGRAPH") presoaked in 20X SSC using a slot blot apparatus (BRL). To neutralize the bound DNA, slots were washed twice with 0.5 ml of 1M Tris, pH 7.2/2M NaCl and once with 0.5 ml of 20X SSC. The filters were removed, washed briefly in 2X SSC. The filters were removed, washed briefly in 2X SSC and UV crosslinked (Stratalinker, Strategene) prior to hybridization with the full length HBV probe (see above).

(iv) Results

The presence of HBV DNA as relaxed circle, replication intermediate (single-stranded DNA and partial relaxed circle), and integrated HBV DNA was quantitatively compared in antiviral oligonucleotide-treated 2.2.15 cells. The relative amounts of relaxed circle DNA and replicative intermediates were normalized to the amounts of integrated DNA because the levels of integrated DNA should not be affected by antiviral treatment. The results were plotted out as a percent of the untreated control.

As shown in Table 1, the ID$_{50}$ (dose necessary to inhibit 50% of the viral activity as compared with control) of DRII(S) (SEQ ID NO: 2), Pre-S1 (SID NO: 4), Loop (SEQ ID NO: 5), p-AUG (SID NO: 3), and Between (SEQ ID NO: 7) ranged from 10 μM to as little as <5 μM (i.e., from 1–5 μM) for DRII(S). This demonstrates that HBV replication is substantially inhibited by even small amounts of the antiviral oilgonucleotides of the invention.

TABLE 1

| ANTIVIRAL OLIGONUCLEOTIDE | ID$_{50}$ |
|---|---|
| DRII(S) | <5 μM |
| pre-S1 | 4 μM |
| Loop | 7 μM |
| p-AUG | 9 μM |
| Between | 10 μM |
| DRII(R) | 20 μM |

EXAMPLE 2

Antiviral Assay Using Poly- or Oligonucleotides Delivered to Cells in the Form of a Soluble Molecular Complex (i) Formation of soluble molecular complexes containing antiviral poly- or oligonucleotides Soluble molecular complexes for delivering the antiviral oligonucleotides, DRII(S) (SEQ ID NO: 2), Loop (SID NO: 5), and Between (SID NO: 7) (described in Example 1), to hepatocytes were produced as follows.

A carrier conjugate was formed by chemically linking asialoorosomucoid to polylysine via a peptide bond. The linkage was formed with a water soluble carbodiimide as described by Jung, G. et al. (1981) Biochem. Biophys. Res. Commun. Vol. 101: 599–606.

In order to prepare the carrier for linkage with oligos DRII(S), Loop, and Between (ranging from 21 to 25 bases in length) oligonucleotide and carrier solutions were made as follows. To form the oligo solution, the oligo was prepared to a concentration of 40 mg/ml in 1x tris-EDTA (TE). 3 μl of this 40 mg/ml oligo solution was then diluted with 6 μl 4M NaCl and 71 μl H$_2$O. This yielded an oligo solution of 1.50 mg/ml in 0.3M NaCl. To form the carrier solution, the carrier was prepared to 40 mg/ml in H$_2$O. 10 μl of this 40 mg/ml conjugate solution was then diluted with 70 μl H$_2$O. This yielded a carrier solution of 5.00 mg/ml.

The optimal ratio of oligo:carrier for forming a soluble molecular complex was then determined by Gel Retardation Assay (GRA) as follows. Gels were prepared by dissolving 1.2 g low-melting agarose in 30 ml 1xtris-phosphate-EDTA (TPE) buffer with stirring and heating. The solution was allowed to cool, followed by addition of 3 μl of ethydium bromide (EtBr) just prior to casting the gel. The gel was then poured into a gel caster. Two combs were positioned in the in gel and it was allowed to solidify for about 30 minutes.

Using the 1.50 mg/ml oligo solution and the 5.00 mg/ml carrier solution, 8 μl of oligo (12 μg) was diluted with a range of carrier volumes up to 8 μl (40 μg). H$_2$O was added to the oligo-carrier solution to give a final volume of 16 μl. 3 μl of 6xsucrose-bromophenol blue sample buffer was then added to every sample. To run these samples in the prepared gel, 15 μl of each oligo-carrier sample was added per lane. The gel was then covered in 1x TPE and run at 100 volts constant voltage for 30 min. To determine at what ratio of carrier to oligo the migration of the oligo in the gel becomes fully retarded, the gel was examined under UV lighting. This is the optimal carrier:oligo binding ratio.

After determination of the optimal carrier:oligo binding ratio, formation of a soluble complex comprised of the two was performed as follows. Using the 40 mg/ml oligo solution and the 40 mg/ml carrier solution, the volume of carrier necessary to give the carrier:oligo ratio as determined in step III above for a total of 7.6 mg oligo (190 μl) was calculated.

The volume of 4M NaCl necessary to give a final NaCl concentration of 0.15M in the complex solution was also then calculated. (The formula, x=y (0.039), where y=oligo volume+carrier volume, can be used to calculate the 4M NaCl volume needed in the event a final complex target volume is not known). The calculated volume of 4M NaCl was next added to 190 µl of oligo and mixed well. A small amount of $H_2O$ was added to achieve the specific complex target volume. While gently vortexing, the calculated volume of conjugate was then added to the oligo-NaCl mixture. The mixture was allowed to stand at room temperature for 10 minutes for complete complex formation. 1.5 µl of the complex was then diluted with 14.5 µl $H_2O$ and 3 µl 6×sucrose-bromophenol blue sample buffer. 15 µl of this solution was then loaded onto an agarose gel and run at 100 volts constant voltage for 30 minutes. The gel was examined under UV lighting to verify that the oligo had been completely complexed.

In order to determine the concentration of complex, the following was performed. 5 µl of the 40 mg/ml oligo solution was diluted with 5.000 ml $H_2O$. 5 µl of the complex was then diluted with 1.25 ml $H_2O$ and filtered through a 0.45 µm filter. 5 µl of the filtered complex was diluted with 1.25 ml $H_2O$. All three samples were then scanned in a spectrophotometer from 200–400 nm using 5 µl 1×TE in 5.000 ml $H_2O$ as a blank. An extinction coefficient at 260 nm in µg/ml/AU was calculated for the 40 mg/ml oligo solution. Using this extinction coefficient, the concentration of the complex both before and after filtration was then calculated.

Soluble molecular complexes containing other antiviral poly- or oligonucleotides of the present invention can also be formed according to the above-described protocol.

(ii) Antiviral Assay

The soluble molecular complexes described in subsection (i) (containing antiviral oligonucleotides DRII(S) (SEQ ID NO: 2), Loop (SEQ ID NO: 5), and Between (SEQ ID NO: 7)) were assayed for antiviral activity according to the procedure described in Example 1. Molecular complexes containing other antiviral oligonuceotides of the present invention can also be assayed for antiviral activity according to this procedure.

(iii) Results

The presence of extracellular HBV DNA released into the medium was quantitatively compared in 2.2.15 cells treated with soluble molecular complexes containing antiviral oligonucleotides DRII(S) (SEQ ID NO: 1), Loop (SEQ ID NO: 5), and Between (SEQ ID NO: 7). The results were plotted out as a percent of the untreated control (FIG. 3).

As shown in Table 2, the $ID_{50}$s (dose necessary to inhibit 50% of the viral activity as compared with untreated control) of complexes containing DRII(S) (SEQ ID NO: 1), Loop (SEQ ID NO: 5), and Between (SEQ ID NO: 7) were approximately 5 µM, 1 µM, and 2 µM, respectively, as compared with the $ID_{50}$s of free oligos DRII(S), Loop, and Between, which were <5 µM, 7 µM, and 10 µM, respectively. This demonstrates that delivery of the antiviral poly- or oligonucleotides of the present invention to cells infected with HBV can be enhanced when the poly- or oligonucleotides are in the form of a soluble molecular complex of the invention.

TABLE 1

| OLIGONUCLEOTIDE COMPLEXES | $ID_{50}$ |
| --- | --- |
| DRII(S) | 5 µM |
| Between | 2 µM |
| Loop | 1 µM |

EQUIVALENTS

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A soluble molecular complex comprising a poly- or oligonucleotide which hybridizes to an RNA primer-binding region of a hepatitis B viral nucleic acid or to a hepatitis B viral RNA primer, wherein the poly- or oligonucleotide is complexed with a carrier comprised of a cell-specific binding agent and a poly- or oligonucleotide-binding agent.

2. The soluble molecular complex of claim 1, wherein the poly- or oligonucleotide-binding agent is polylysine.

3. The soluble molecular complex of claim 1, wherein the cell-specific binding agent is a ligand for the asialoglycoprotein receptor and the targeted cell is an hepatocyte.

4. The soluble molecular complex of claim 1, wherein the viral nucleic acid is a DRII region of hepatitis B virus DNA.

5. The soluble molecular complex of claim 4, wherein the poly- or oligonucleotide comprises the nucleotide sequence shown in SEQ ID NO: 1.

6. The soluble molecular complex of claim 1, wherein the RNA primer binds to a DRII region of hepatitis B virus DNA.

7. The soluble molecular complex of claim 6, wherein the poly- or oligonucleotide comprises the nucleotide sequence shown in SEQ ID NO: 2.

8. A soluble molecular complex comprising a poly- or oligodeoxyribonucleotide which hybridizes to the DRII region of hepatitis B virus DNA complexed with a carrier comprised of a ligand for the asialoglycoprotein receptor and polylysine.

9. The soluble molecular complex of claim 8, wherein the poly- or oligodeoxyribonucleotide comprises the nucleotide sequence shown in SEQ ID NO: 1.

10. A soluble molecular complex comprising a poly- or oligodeoxyribonucleotide which hybridizes to an RNA primer having the function of binding to the DRII region of hepatitis B virus DNA, complexed with a carrier comprised of a ligand for the asialoglycoprotein receptor and polylysine.

11. The soluble molecular complex of claim 10, wherein the poly- or oligodeoxyribonucleotide comprises the nucleotide sequence shown in SEQ ID NO: 2.

12. A soluble molecular complex comprising a poly- or oligonucleotide which hybridizes to an encapsidation signal of a hepatitis B viral mRNA, wherein the poly- or oligonucleotide is complexed with a carrier comprised of a cell-specific binding agent and a poly- or oligonucleotide-binding agent.

13. The soluble molecular complex of claim 12, wherein the poly- or oligonucleotide-binding agent is polylysine.

14. The soluble molecular complex of claim 12, wherein the cell-specific binding agent is a ligand for the asialoglycoprotein receptor and the targeted cell is an hepatocyte.

15. The soluble molecular complex of claim 12, wherein the encapsidation signal is a hepatitis B virus $\epsilon$ cis-encapsidation signal.

16. The soluble molecular complex of claim 12, wherein the poly- or oligonucleotide comprises the nucleotide sequence shown in SEQ ID NO: 5.

17. The soluble molecular complex of claim 12, wherein the poly- or oligonucleotide comprises the nucleotide sequence shown in SEQ ID NO: 6.

18. The soluble molecular complex of claim 12, wherein the poly- or oligonucleotide comprises the nucleotide sequence shown in SEQ ID NO: 7.

19. The soluble molecular complex of claim 12, wherein the poly- or oligonucleotide comprises the nucleotide sequence shown in SEQ ID NO: 8.

20. A soluble molecular complex comprising a poly- or oligodeoxyribonucleotide which hybridizes to a hepatitis B virus $\epsilon$ cis-encapsidation signal mRNA complexed with a carrier comprised of a ligand for the asialoglycoprotein receptor and polylysine.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

GCAGAGGTGA AGCGAAGTGC ACACG 25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear     ( i i ) MOLECULE TYPE: cDNA ( x i ) SEQUENCE DESCRIPTION: SEQ ID NO:2:

CGTGTGCACT TCGCTTCACC TCTGC 25

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:3:

GATAGGGGCA TTTGGTGGTC T 21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:4:

CCCATGCTGT AGATCTTGTT C 21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:5:

GCCCCAAAGC CACCCAAGGC A 21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:6:

TTGAACAGTG GGACATGTAC A 21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:7:

CACAGCTTGG AGGCTTGAAC A 21

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

ATGTCCATGC CCCAAAGCCA C  21

(2) INFORMATION FOR SEQ ID NO:9:

(i) SEQUENCE CHARACTERISTICS:
(A) LENGTH: 81 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO:9:

UGUUCAUGUC CUACUGUUCA AGCCUCCAAG CUGUGCCUUG GGUGGCUUUG GGGCAUGGAC  60

AUCGACCCUU AUAAAGAAUU U  81